United States Patent [19]
TenBrink

[11] Patent Number: 4,894,437
[45] Date of Patent: Jan. 16, 1990

[54] NOVEL RENIN INHIBITING POLYPEPTIDE ANALOGS CONTAINING S-ARYL-D- OR L- OR DL-CYSTEINYL, 3-(ARYLTHIO)LACTIC ACID OR 3-(ARYLTHIO)ALKYL MOIETIES

[75] Inventor: Ruth E. TenBrink, Kalamazoo, Mich.

[73] Assignee: The Upjohn Company, Kalamazoo, Mich.

[21] Appl. No.: 85,674

[22] PCT Filed: Oct. 21, 1986

[86] PCT No.: PCT/US86/02227
§ 371 Date: Jun. 29, 1987
§ 102(e) Date: Jun. 29, 1987

[87] PCT Pub. No.: WO87/02986
PCT Pub. Date: May 21, 1987

Related U.S. Application Data

[63] Continuation of Ser. No. 798,459, Nov. 15, 1985, abandoned.

[51] Int. Cl.$^4$ .................. C07K 7/06; A61K 37/43; C07C 101/30
[52] U.S. Cl. .................. 530/328; 530/329; 530/330; 530/331; 530/800; 560/39
[58] Field of Search ............. 530/328, 329, 330, 331, 530/300, 800; 514/11; 560/39

[56] References Cited

U.S. PATENT DOCUMENTS

| 4,424,207 | 1/1984 | Szelke et al. ................ 424/177 |
| 4,470,971 | 9/1984 | Boger et al. ................ 424/177 |
| 4,477,440 | 10/1984 | Boger et al. ................ 530/328 |
| 4,477,441 | 10/1984 | Boger et al. ................ 530/328 |
| 4,478,826 | 10/1984 | Veber et al. ................ 424/177 |
| 4,478,827 | 10/1984 | Haber et al. ................ 424/177 |
| 4,479,941 | 10/1984 | Veber et al. ................ 424/177 |
| 4,485,099 | 11/1984 | Boger et al. ................ 424/177 |
| 4,514,332 | 4/1985 | Hansen, Jr. et al. .......... 530/330 |
| 4,548,926 | 10/1985 | Matsueda et al. ............. 530/800 |
| 4,595,677 | 6/1986 | Riniker et al. .............. 530/331 |
| 4,613,676 | 9/1986 | Fuhrer et al. ............... 560/39 |
| 4,618,600 | 10/1986 | Johnson et al. .............. 530/325 |
| 4,636,491 | 1/1987 | Bock et al. ................. 530/300 |
| 4,645,759 | 2/1987 | Luly et al. ................. 530/331 |
| 4,652,551 | 3/1987 | Luly et al. ................. 530/331 |
| 4,661,473 | 4/1987 | Boger et al. ................ 530/329 |
| 4,663,310 | 5/1987 | Bock et al. ................. 530/330 |
| 4,668,770 | 5/1987 | Boger et al. ................ 530/331 |
| 4,698,329 | 10/1987 | Matsueda et al. ............. 530/331 |
| 4,719,288 | 1/1988 | Fuhrer et al. ............... 530/331 |
| 4,727,060 | 2/1988 | Buhlmayer et al. ............ 530/332 |
| 4,743,584 | 5/1988 | Boger ....................... 514/11 |

FOREIGN PATENT DOCUMENTS

| 0045665 | 2/1982 | European Pat. Off. . |
| 0045161 | 3/1982 | European Pat. Off. . |
| 0053017 | 6/1982 | European Pat. Off. . |
| 0077028 | 4/1983 | European Pat. Off. . |
| 0077029 | 4/1983 | European Pat. Off. . |
| 0081783 | 4/1983 | European Pat. Off. . |
| 0104041 | 3/1984 | European Pat. Off. . |
| 0111266 | 6/1984 | European Pat. Off. . |
| 0114993 | 6/1984 | European Pat. Off. . |
| 0118223 | 9/1984 | European Pat. Off. . |
| 0143746 | 6/1985 | European Pat. Off. . |
| 0156322 | 10/1985 | European Pat. Off. . |
| 0157409 | 10/1985 | European Pat. Off. . |
| 0173481 | 3/1986 | European Pat. Off. . |
| 84/03044 | 8/1984 | PCT Int'l Appl. . |
| 2045771 | 11/1980 | United Kingdom . |

OTHER PUBLICATIONS

Holladay, et al., "Synthesis of Hydroxyethylene and Ketomethylene Dipeptide Isosteres", Tetrahedron Letters, vol. 24, No. 41, pp. 4401–4404, 1983.
Chem. Abstracts, vol. 98, No. 25, Jun. 20, 1983, p. 597, abstract 215980d, Kurihara, Tozaburo et al., "Studies on Antibacterial Peptide, XVII, Synthesis and Antibacterial Activity of Cyclic α–Acylpentapeptides Relayed to Colistin".

Primary Examiner—Delbert R. Phillips
Attorney, Agent, or Firm—Lawrence T. Welch

[57] ABSTRACT

The present invention provides novel renin-inhibiting peptides of the formula X-$A_6$-$B_5$-$C_8$-$D_9$-$E_{10}$-$F_{11}$-$G_{12}$-$H_{13}$-$I_{14}$-Z, wherein X and Z are terminal groups, $C_8$ contains S-aryl-D- or L- or DL-cysteinyl, 3-(arylthio)-lactic acid, and 3-(arylthio)alkyl moieties, and the remaining variables are amino acid residues. Such inhibitors are useful for the diagnosis and control of renin-dependent hypertension.

6 Claims, No Drawings

NOVEL RENIN INHIBITING POLYPEPTIDE ANALOGS CONTAINING S-ARYL-D- OR L- OR DL-CYSTEINYL, 3-(ARYLTHIO)LACTIC ACID OR 3-(ARYLTHIO)ALKYL MOIETIES

This application is a continuation of application Ser. No. 798,459, filed on Nov. 15, 1985, now abandoned.

BACKGROUND OF THE INVENTION

The present invention provides novel compounds. More particularly, the present invention provides novel renin-inhibiting peptide analogs. Most particularly, the present invention provides renin-inhibitory compounds having S-aryl-D- or L- or DL-cysteinyl, 3-(arylthio)lactic acid or 3-(arylthio)alkyl moieties at the 8 position (as compared to the renin substrate described below). The renin inhibitors provided herein are useful for the diagnosis and control of renin-dependent hypertension.

Renin is an endopeptidase which specifically cleaves a particular peptide bond of its substrate (angiotensinogen), of which the N-terminal sequence in equine substrate is for example:

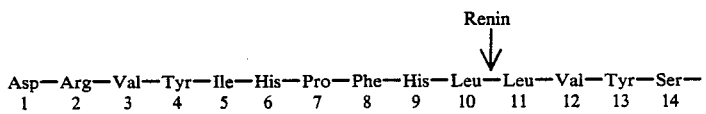

as found by L. T. Skeggs et al, J. Exper. Med. 106, 439 (1957). Human renin substrate has a different sequence as recently discovered by D. A. Tewkesbury et al, Biochem. Biophys. Res. Comm. 99, 1311 (1981). It may be represented as follows:

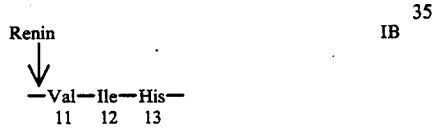

and having the sequence to the left of the arrow ($\downarrow$) being as designated in formula IA above.

Renin cleaves angiotensinogen to produce angiotensin I, which is converted to the potent pressor angiotensin II. A number of angiotensin I converting enzyme inhibitors are known to be useful in the treatment of hypertension. Inhibitors of renin are also useful in the treatment of hypertension.

INFORMATION DISCLOSURE

A number of renin-inhibitory peptides have been disclosed. Thus, U.S. Pat. No. 4,424,207, and European published applications 45,665 and 104,041 disclose certain peptides with the dipeptide at the 10,11-position containing an isostere bond. A number of statine derivatives stated to be renin inhibitors have been disclosed, see, e.g., European published applications 77,028; 81,783; and 114,993; and U.S. Pat. Nos. 4,478,826; 4,470,971 and 4,479,941. Terminal disulfide cycles have also been disclosed in renin inhibiting peptides; see, e.g., U.S. Pat. Nos. 4,477,440 and 4,477,441. Aromatic and aliphatic amino acid residues at the 10,11 position of the renin substrate are disclosed in U.S. Pat. No. 4,478,827. C-terminal amide cycles are disclosed in U.S. Pat. No. 4,485,099. Certain tetrapeptides are disclosd in European publications 111,266 and 77,027. Further, European published application No. 118,223 discloses certain renin inhibiting peptide analogs where the 10-11 peptide link is replaced by a one to four atom carbon or carbon-nitrogen link. Additionally, Holladay et al., in "Synthesis of Hydroxyethylene and Ketomethylene Dipeptide Isosteres", Tetrahedron Letters, Vol. 24, No. 41, pp. 4401-4404, 1983 disclose various intermediates in a process to prepare stereo-directed "ketomethylene" and "hydroxyethylene" dipeptide isosteric functional groups disclosed in the above noted U.S. Pat. No. 4,424,207.

Additonally, published European Applications 45,161 and 53,017 disclose amide derivatives useful as inhibitors of angiotensin converting enzymes.

SUMMARY OF THE INVENTION

The present invention particularly provides a renin inhibitory peptide of the formula $X\text{-}A_6\text{-}B_7\text{-}C_8\text{-}D_9\text{-}E_{10}\text{-}F_{11}\text{-}G_{12}\text{-}H_{13}\text{-}I_{14}\text{-}Z$, wherein X is
(a) hydrogen,
(b) $C_1\text{-}C_5$alkyl
(c) $R_5\text{—O—CH}_2\text{—C(O)—}$,
(d) $R_5\text{—CH}_2\text{—O—C(O)—}$,
(e) $R_5\text{—O—C(O)—}$,

IA (f) $R_5\text{—(CH}_2)_n\text{—C(O)—}$,
(g) $R_4N(R_4)\text{—(CH}_2)_n\text{—C(O)}$,
(h) $R_5\text{—SO}_2\text{—(CH}_2)_q\text{—C(O)—}$,
(i) $R_5\text{—SO}_2\text{—(CH}_2)_q\text{—O—C(O)—}$, or
(j) $R_6\text{—(CH}_2)_i\text{—C(O)—}$;

wherein $A_6$ is absent or a divalent moiety of the formula $XL_1$, $XL_2$, or $XL_{2a}$ wherein $B_7$ is absent or a divalent moiety of the formula $XL_b$ wherein $C_8$ is absent or a divalent moiety of the formula $XL_1$ or $XL_2$, wherein $D_9$ is absent or a divalent moiety of the formula $XL_3$ or $XL_{2a}$, wherein $E_{10}\text{-}F_{11}$ is a divalent moiety of the formula $XL_6$, $XL_{6a}$, $XL_{6b}$, $XL_{6c}$, $XL_{6d}$, or $XL_{6e}$, wherein * indicates an asymmetric center which is either in the R or S configuration;

wherein $G_{12}$ is absent or a divalent moiety of the formula $XL_4$ or $XL_{4a}$ wherein $H_{13}$ is absent or a divalent moiety of the formula $XL_4$ wherein $I_{14}$ is absent or a divalent moiety of the formula $XL_5$ wherein Z is
(a) $\text{—O—R}_{10}$,
(b) $\text{—N(R}_4)R_{14}$, or
(c) $C_4\text{-}C_8$cyclic amino;

wherein R is
(a) isopropyl,
(b) isobutyl,
(c) phenylmethyl, or
(d) $C_3\text{-}C_7$cycloalkyl;

wherein $R_1$ is
(a) hydrogen,
(b) $C_1\text{-}C_5$alkyl,
(c) aryl,
(d) $C_3\text{-}C_7$cycloalkyl, (e) —Het,
(f) $C_1$-$C_3$alkoxy, or
(g) $C_1$-$C_3$alkylthio;

wherein $R_2$ is
(a) hydrogen, or
(b) —CH($R_3$)$R_4$;

wherein $R_3$ is
(a) hydrogen,
(b) hydroxy,
(c) $C_1$-$C_5$alkyl,
(d) $C_3$-$C_7$cycloalkyl,
(e) aryl,
(f) —Het,
(g) $C_1$-$C_3$alkoxy, or
(h) $C_1$-$C_3$alkylthio;

wherein $R_4$ at each occurrence is the same or different and is
(a) hydrogen, or
(b) $C_1$-$C_5$alkyl;

wherein $R_5$ is
(a) $C_1$-$C_6$alkyl,
(b) $C_3$-$C_7$cycloalkyl,
(c) aryl,
(d) —Het, or
(e) 5-oxo-2-pyrrolidinyl;

wherein $R_6$ is
(a) —S—aryl,
(b) —S—$C_3$-$C_7$cycloalkyl, or
(c) —S—$C_1$-$C_6$alkyl;

wherein $R_7$ is
(a) hydrogen,
(b) $C_1$-$C_5$alkyl,
(c) hydroxy,
(d) amino $C_1$-$C_4$alkyl—,
(e) guanidinyl $C_1$-$C_3$alkyl—,
(f) aryl,
(g) —Het,
(h) methylthio,
(i) $C_3$-$C_7$cycloalkyl, or
(j) amino;

wherein $R_8$ is
(a) hydrogen,
(b) $C_1$-$C_5$alkyl,
(c) hydroxy,
(d) aryl,
(e) —Het,
(f) guanidinyl $C_1$-$C_3$alkyl—, or
(g) $C_3$-$C_7$cycloalkyl;

wherein $R_9$ is
(a) hydrogen,
(b) hydroxy,
(c) amino $C_1$-$C_4$alkyl—, or
(d) guanidinyl $C_1$-$C_3$alkyl—;

wherein $R_{10}$ is
(a) hydrogen,
(b) $C_1$-$C_5$alkyl,
(c) —(CH$_2$)$_n$R$_{16}$,
(d) —(CH$_2$)$_n$R$_{17}$,
(e) $C_3$-$C_7$cycloalkyl,
(f) a pharmaceutically acceptable cation,
(g) —(CHR$_{25}$)—CH$_2$—R$_{15}$, or
(h) —CH$_2$—(CHR$_{12}$)—R$_{15}$;

wherein $R_{11}$ is —R or —$R_2$;
wherein $R_{12}$ is —(CH$_2$)$_n$—R$_{13}$;
wherein $R_{13}$ is
(a) aryl,
(b) amino,
(c) mono-, di or tri-$C_1$-$C_3$alkylamino,
(d) —Het,
(e) $C_1$-$C_5$alkyl
(f) $C_3$-$C_7$cycloalkyl,
(g) $C_1$-$C_5$alkenyl,
(h) $C_3$-$C_7$cycloalkenyl,
(i) hydroxy,
(j) $C_1$-$C_3$alkoxy,
(k) $C_1$-$C_3$alkanoyloxy,
(l) mercapto,
(m) $C_1$-$C_3$alkylthio,
(n) —COOH,
(o) —CO—O—$C_1$-$C_6$alkyl,
(p) —CO—O—CH$_2$—($C_1$-$C_3$alkyl)—N($C_1$-$C_3$alkyl)$_2$,
(q) —CO—NR$_{22}$R$_{26}$;
(r) $C_4$-$C_7$cyclic amino,
(s) $C_4$-$C_7$cycloalkylamino,
(t) guanidyl,
(u) cyano,
(v) N-cyanoguanidyl,
(w) cyanoamino,
(x) (hydroxy $C_2$-$C_4$alkyl)amino, or
(y) di-(hydroxy$C_2$-$C_4$alkyl)amino;

wherein $R_{14}$ is
(a) hydrogen,
(b) $C_1$-$C_{10}$alkyl,
(c) —(CH$_2$)$_n$—R$_{18}$,
(d) —(CH$_2$)$_n$—R$_{19}$,
(e) —(CHR$_{25}$)—CH$_2$—R$_{15}$,
(f) —CH$_2$—(CHR$_{12}$)—R$_{15}$,
(g) (hydroxy $C_1$-$C_8$alkyl), or
(h) ($C_1$-$C_3$alkoxy)$C_1$-$C_8$alkyl;

wherein $R_{15}$ is
(a) hydroxy,
(b) $C_{3L}$-$C_7$cycloalkyl,
(c) aryl,
(d) amino,
(e) mono-, di-, or tri- $C_1$-$C_3$alkylamino,
(f) mono- or di-[hydroxy $C_2$-$C_4$alkyl]amino,
(g) —Het,
(h) $C_1$-$C_3$alkoxy—,
(i) $C_1$-$C_3$alkanoyloxy—,
(j) mercapto,
(k) $C_1$-$C_3$alkylthio—,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;

wherein $R_{16}$ is
(a) aryl,
(b) amino,
(c) mono- or di- $C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;

wherein $R_{17}$ is
(a) —Het,
(b) $C_1$-$C_5$alkenyl,
(c) $C_3$-$C_7$cycloalkenyl,
(d) $C_1$-$C_3$alkoxy,
(e) mercapto,
(f) $C_1$-$C_3$alkylthio,
(g) —COOH,
(h) —CO—O—$C_1$-$C_6$alkyl,
(i) —CO—O—CH$_2$—($C_1$-$C_3$alkyl)—N($C_1$-$C_3$alkyl)$_2$, (j) —CO—NR$_{22}$R$_{26}$,
(k) tri-C$_1$-C$_3$alkylamino,
(l) guanidyl,
(m) cyano,
(n) N-cyanoguanidyl,
(o) (hydroxy C$_2$-C$_4$alkyl)amino, or
(p) di-(hydroxy C$_2$-C$_4$alkyl)amino;

wherein R$_{18}$ is
(a) amino,
(b) mono-, or di- C$_1$-C$_3$alkylamino, or
(c) C$_4$-C$_7$cyclic amino;

wherein R$_{19}$ is
(a) aryl,
(b) —Het,
(c) tri-C$_1$-C$_3$alkylamino,
(d) C$_3$-C$_7$cycloalkyl,
(e) C$_1$-C$_5$alkenyl,
(f) C$_3$-C$_7$cycloalkenyl,
(g) hydroxy,
(h) C$_1$-C$_3$alkoxy,
(i) C$_1$-C$_3$alkanoyloxy,
(j) mercapto,
(k) C$_1$-C$_3$alkylthio,
(l) —COOH,
(m) —CO—O—C$_1$-C$_6$alkyl,
(n) —CO—O—CH$_2$—(C$_1$-C$_3$alkyl)—N(C$_1$-C$_3$alkyl)$_2$,
(o) —CO—NR$_{22}$R$_{26}$,
(p) C$_4$-C$_7$cycloalkylamino,
(q) guanidyl,
(r) cyano,
(s) N-cyanoguanidyl,
(t) cyanoamino,
(u) (hydroxy C$_2$-C$_4$alkyl)amino,
(v) di-(hydroxy C$_2$-C$_4$alkyl)amino; or
(w) —SO$_3$H;

wherein R$_{20}$ is
(a) hydrogen,
(b) C$_1$-C$_5$alkyl, or
(c) aryl-C$_1$-C$_5$alkyl;

wherein R$_{21}$ is
(a) —NH$_2$, or
(b) —OH;

wherein R$_{22}$ is
(a) hydrogen, or
(b) C$_1$-C$_3$alkyl;

wherein R$_{23}$ is
(a) —(CH$_2$)$_n$—OH,
(b) —(CH$_2$)$_n$—NH$_2$,
(c) aryl, or
(d) C$_1$-C$_3$alkyl;

wherein R$_{24}$ is
(a) —R$_1$,
(b) —(CH$_2$)$_n$—OH, or
(c) —(CH$_2$)$_n$—NH$_2$;

wherein R$_{25}$ is —(CH$_2$)$_n$—R$_{13}$;

wherein R$_{26}$ is
(a) hydrogen,
(b) C$_1$-C$_3$alkyl, or
(c) phenyl-C$_1$-C$_3$alkyl;

wherein i is one to three, inclusive;
wherein m is one or two;
wherein for each occurrence n is independently an integer of zero to five, inclusive;
wherein p is zero to 2 inclusive;
wherein q is 1 to 5, inclusive;
wherein Q is
(a) —CH$_2$—,
(b) —CH(OH)—,
(c) —O—, or
(d) —S—; and wherein M is
(a) —CO—, or
(b) —CH$_2$—;

wherein aryl is phenyl or naphthyl substituted by zero to 3 to the following:
(a) C$_1$-C$_3$alkyl,
(b) hydroxy,
(c) C$_1$-C$_3$alkoxy,
(d) halo,
(e) amino,
(f) mono- or di-C$_1$-C$_3$alkylamino,
(g) —CHO,
(h) —COOH,
(i) COOR$_{26}$,
(j) CONHR$_{26}$,
(k) nitro,
(l) mercapto,
(m) C$_1$-C$_3$alkylthio,
(n) C$_1$-C$_3$alkylsulfinyl,
(o) C$_1$-C$_3$alkylsulfonyl,
(p) —N(R$_4$)—C$_1$-C$_3$alkylsulfonyl,
(q) SO$_3$H,
(r) SO$_2$NH$_2$,
(s) —CN, or
(t) —CH$_2$NH$_2$;

wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:

(i) C$_1$-C$_6$alkyl,
(ii) hydroxy,
(iii) trifluoromethyl,
(iv) C$_1$-C$_4$alkoxy,
(v) halo,
(vi) aryl,
(vii) aryl C$_1$-C$_4$alkyl—,
(viii) amino, and
(ix) mono- or di-C$_1$-C$_4$alkylamino;

with the overall provisos that
(1) X is R$_6$—(CH$_2$)$_i$—C(O)—only when A$_6$, B$_7$, and C$_8$ are absent;
(2) R$_{18}$ or R$_{19}$ is hydroxy, mercapto, or amino, or a mono-substituted nitrogen containing group bonded through the nitrogen only when n is not one;
(3) R$_{12}$ is —(CH$_2$)$_n$—R$_{13}$ and n is zero and both R$_{13}$ and R$_{15}$ are oxygen-, nitrogen-, or sulfur-containing substituents bonded through the hetero atom, only when the hetero atom is not also bonded to hydrogen;
(4) R$_{25}$ is —(CH$_2$)$_n$—R$_{13}$ and n is zero only when R$_{13}$ is other than a primary or secondary nitrogen-containing group hydroxy or mercapto group or when R$_4$ of —N(R$_4$)R$_{14}$ is other than hydrogen; and
(5) R$_{17}$ or R$_{19}$ is —COOH only when n for that moiety is other than zero;
(6) R$_{16}$ or R$_{17}$ is an amino-containing substituent, hydroxy, mercapto, or —Het bonded through the hetero atom only when n for that substituent is an integer from two to five, inclusive; and (7) when $R_{12}$ is $-(CH_2)_n-R_{13}$ and n is zero, then $R_{13}$ and $R_{15}$ cannot both be $-COOH$;

or a carboxy-, amino-, or other reactive group-protected form or a pharmaceutically acceptable acid addition salt thereof.

These compounds are shown in relation to the human renin substrate as follows:

$$\begin{array}{cccccccc} 6 & 7 & 8 & 9 & 10 & 11 & 12 & 13 \\ -His & Pro & Phe & His & Leu & Val & Ile & His- \\ X \quad A_6 & B_7 & C_8 & D_9 & E_{10} & F_{11} & G_{12}H_{13} & I_{14} \quad Z, \end{array}$$

The present invention provides peptide inhibitors of renin which contain modification of the $Phe^8$ (angiotensinogen numbering) position. These modifications involve the insertion of a heteroatom-containing fragment into the side chain of the residue occupying the $Phe^8$ position. These changes in the normal Phe side chain result in dramatic changes in the overall length and size of the side chain. The hetero-atom also alters the polarity, angles, and H-bonding ability of the side chain elements. Additionally, changes in the backbone may be made such as substitution of oxygen for nitrogen in the corresponding α-amino acid. These changes, in addition to being chemically novel to renin inhibitors, also confer stability to the position 8–9 bond to the action of chymotrypsin and elastase due to the lack of fit of the lengthened side chain into the active site pocket of these enzymes.

Examples of pharmaceutically acceptable acid addition salts include: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_4)$alkyl refers to alkyl of one to 4 carbon atoms, inclusive, or methyl, ethyl, propyl, butyl, and isomeric forms thereof. $C_4-C_7$cyclic amino indicates a monocyclic group containing one nitrogen and 4 to 7 carbon atoms.

Examples of $(C_3-C_{10})$cycloalkyl which include alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl, cyclononyl, cyclodecyl and isomeric forms thereof.

Examples of aryl include phenyl, naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4- 2,3,6-, or 2,4,5-)trimethylphenyl, (o- m-, or p-)fluorophenyl, (o-, m-, or p-trifluoromethyl)phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluoro-methylphenyl, (o-, m-, or p-)ethoxyphenyl, (4- or 5-)chloro-2-methoxy-phenyl, and 2,4-dichloro(5- or 6-)methylphenyl.

Examples of -Het include: 2-, 3-, or 4-pyridyl, imidazolyl, indolyl, $N^{in}$-formyl-indolyl, $N^{in}$-$C_2$-$C_5$alkyl-C(O)-indolyl, [1,2,4]-triazolyl, 2-, 4-, or 5-pyrimidinyl, 2- or 3-thienyl, piperidinyl, pyrryl, pyrrolinyl, pyrrolidinyl, pyrazolyl, pyrazolinyl, pyrazolidinyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, thienyl, and benzothienyl. Each of these moieties may be substituted as noted above.

As would be generally recognized by those skilled in the art of organic chemistry, a heterocycle as defined herein for -Het would not be bonded through oxygen or sulfur or through nitrogen which is within a ring and part of a double bond.

Halo is halogen (fluoro, chloro, bromo, or iodo) or trifluoromethyl.

Examples of pharmaceutically acceptable cations include: pharmacologically acceptable metal cations, ammonium, amine cations, or quaternary ammonium cations. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are also within the scope of this invention. Pharmacologically acceptable amine cations are those derived from primary, secondary, or tertiary amines.

The novel peptides herein contain both natural and synthetic amino acid residues. These residues are depicted using standard amino acid abbreviations (see, e.g., Roberts, et al., Basic Principles of Organic Chemistry, pp. 703–705 (New York 1965)) unless otherwise indicated.

All the renin-inhibiting compounds of the present invention may be administered in the conventional forms, such as disclosed in U.S. Pat. No. 4,424,207 which is incorporated by reference herein. Likewise, the amounts disclosed in the U.S. Pat. No. 4,424,207 are examples applicable to the compounds of the present invention.

Preferably, the dosages of the present invention are for oral administration for treatment of humans to effect renin inhibition for the purpose of favorably affecting blood pressure. For this purpose, the compounds are administered from 0.1 mg to 1000 mg per kg per dose, administered from 1 to 4 times daily. Equivalent dosages for other routes of administration are also employed.

The exact dose depends on the age, weight, and condition of the patient and on the frequency and route of administration. Such variations are within the skill of the practitioner or can readily be determined.

The compounds of the present invention may be pharmaceutically acceptable salts both those which can be produced from the free bases by methods well known in the art and those with which acids have pharmacologically acceptable conjugate bases.

The compounds of the present invention are preferably orally administered in the form of pharmacologically acceptable acid addition salts. Preferred pharmacologically acceptable salts for oral administration include the citrate and aspartate salts, although any pharmacologically acceptable salt is useful in this invention, including those listed above. These salts may be in hydrated form.

The compounds of the present invention are prepared as depicted in the charts and as described more fully in the Preparations and Examples.

The description below refers to the structures depicted on the formula page and in the Charts A–E. In those formulas, all variables are as defined above except where noted.

Generally, the renin inhibiting polypeptides may be prepared by either polymer assisted or solution phase peptide synthetic procedures analogous to those described hereinafter or to those methods known in the art. For example, the carboxylic moiety of $N^\alpha$-t-butyloxycarbonyl (Boc)-substituted amino acid derivatives having suitable side chain protecting groups, if necessary, may be condensed with the amino functionality of a suitably protected amino acid, peptide or polymer-bound peptide using a conventional coupling protocol such as dicyclohexylcarbodiimide (DCC) and 1-hydroxybenzotriazole (HOBT) in methylene chloride or dimethylformamide. The synthetic procedures used to incorporate the novel moieties herein are also described, for example, in U.S. Pat. Nos. 4,424,207; 4,470,971; 4,477,440; 4,477,441; 4,478,826; 4,478,827; 4,479,941; and 4,485,099, and copending application Ser. No. 753,198, filed 9 July 1985, all of which are expressly incorporated by reference herein. See, also, published European patent applications 45,161; 45,665; 53,017; 77,028; 77,029; 81,783; 104,041; 111,266; 114,993; and 118,223.

Following coupling reaction completion, the $N^\alpha$-Boc moiety may be selectively removed with 45% trifluoroacetic acid/2% anisole (v/v) in methylene chloride. Neutralization of the resultant trifluoroacetate salt may be accomplished with 10% diisopropylethylamine in methylene chloride. In the case of polymer-assisted peptide synthesis, this stepwise, coupling strategy may be partially or completely automated to provide the desired peptide-polymer intermediates. Anhydrous hydrofluoric acid treatment of the peptide-polymer intermediate may then be used to effect simultaneous protecting group removal and cleavage of the peptide from its polymeric support. A notable exception to this includes $N^{in}$-formyl-indolyl-substituted peptides in which the $N^{in}$-formyl-indolyl moiety is stable to TFA or HF but may be removed by $NH_3$ or NaOH. Because FTrp is somewhat unstable to base in synthetic procedures, possibly causing lower yields, it may be desirable in solution phase synthesis to introduce the FTrp-containing moiety late in the synthetic sequence so that it is not exposed to such conditions.

The incorporation of $N^{in}$-formyl-Trp into compounds of the present invention is easily accomplished because of the commercial availability of $N^\alpha$-Boc-$N^{in}$-formyl-Trp-OH. However, the $N^{in}$-formyl moiety may be introduced into indolyl-substituted amino acid derivatives or related compounds by reaction with HCl-formic acid as reported in the literature, see A. Previero et al, Biochim. Biophys.Acta 147, 453 (1967); Y. C. S. Yang et al, Int. J. Peptide Protein Res. 15, 130 (1980).

Generally, methods of alkylation useful in alkylating histidine for use in the present invention are found in Cheung, S. T. et al, Can. J. Chem., Vol 55, pp. 906–910 (1977). However it is now found that in Cheung, S. T. et al, methods it is critical that the reaction conditions for the alkylation of histidine be anhydrous. Further, it is now found also that during work-up instead of adding water directly to the reaction mixture, it is preferred that a buffered aqueous solution be added to the reaction mixture, for example, aqueous sodium or potassium hydrogen sulfate.

This is analogous to that found in Cheung, S. T. et al, Can. J. Chem. Vol 55, pp. 906–910 (1977)), however, it has been found that the process requires anhydrous reaction conditions which are not taught by Cheung et al.

Variations in the above description for starting materials, reactants, reaction conditions and required protecting groups to obtain other such N-alkylated compounds are known to an ordinarily skilled chemist or are readily available in the literature.

These peptides may also be prepared by the standard solid phase techniques of Merrifield. Appropriate protecting groups, reagents, and solvents for both the solution and solid phase methods can be found in "The Peptides: Analysis, Synthesis, and Biology," Vols. 1–5, eds. E. Gross and T. Meienhofer, Academic Press, NY, 1979–1983.

The compounds of the present invention may be in either free form or in protected form at one or more of the remaining (not previously protected) peptide, carboxyl, amino, hydroxy, or other reactive groups. The protecting groups may be any of those known in the polypeptide art. Examples of nitrogen and oxygen protection groups are set forth in T. W. Greene, Protecting Groups in Organic Synthesis, Wiley, N.Y., (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (Boc), benzyloxycarbonyl, acetyl, allyl, phthalyl, benzyl, benzoyl, trityl and the like.

In general, the processes of the present invention may be carried out in the following manner.

The synthesis of the key intermediate, Boc-(R,S)-3-(phenylthio)alanine, is shown in Chart A. This synthesis follows the method of G. Glynn and D. Beight, Tet. Lett.; 25: 2655 (1984). Boc-Serine (Boc-D,L-Ser may be used as chirality is lost at a later step) is converted to its methyl ester using a five-fold excess of methyl iodide and two equivalents of $NaHCO_3$ in DMF as solvent. The alcohol (A-2) is then converted to the mesylate with methanesulfonyl chloride and 1 equiv. of $Et_3N$ in $CH_2Cl_2$. Addition of a second equivalent of $Et_3N$ gives the elimination product A-3. Compound A-3 is stirred with 1.1 equivalents of thiophenol and a catalytic amount of $Et_3N$ in MeOH to give A-4. Hydrolysis of the methyl ester with aq. NaOH in MeOH, followed by acidification, gives Boc-(R,S)-3-(phenylthio)alanine A-5.

The peptides are synthesized by methods known to the art. See, for instance, the series "The Peptides: Analysis, Synthesis, Biology, Vols. 1–5, eds. E. Gross and J. Meienhofer, Academic Press, New York, 1979–1983. The assembly of Boc-(R,S)-3-(phenylthio)alanylHis-Leu [CH(OH)CH$_2$]Val-Ile-2-(amidomethyl)pyridine is shown in Chart B. Boc-Ile and 2-(aminomethyl)pyridine (both commercially available) are coupled using DCC in $CH_2Cl_2$ and aq. $NaHCO_3$ to give B-3. Boc-Leu [CH(OTBDMS)-CH$_2$]Val-OH is coupled to Ile-AMP (AMP-2-(amidomethyl)pyridine) using DEPC (diethyl cyanophosphonate) and $Et_3N$ in CH$_2$Cl$_2$ to give B-4. The Boc group of B-4 is removed with TFA and CH$_2$Cl$_2$ and the resulting TFA salt is neutralized by extraction with CH$_2$Cl$_2$ and aq. NaHCO$_3$. Leu ¥ [CH(OTBDMS)-CH$_2$]Val-IIe-AMP is coupled with Boc-His(Tos)-OH using DEPC and Et$_3$N in CH$_2$Cl$_2$ to give B-5. The Boc grop and tert.-butyldimethylsilyl group of B-7 are removed with TFA and CH$_2$Cl$_2$. The resulting TFA salt is neutralized via extraction with CH$_2$Cl$_2$ and aq. NaHCO$_3$ to give B-6. Compound B-6 is coupled with Boc-(R,S)-3-(phenylthio)alanine using DCC in CH$_2$Cl$_2$. The tosyl protecting group on the histidine side chain is removed with 1-HOBT and MeOH to give the final product, B-7. In a similar manner, the mercaptide anion of cycloalkyl-SH or alkyl-SH (formed from, for instance, the commercially available mercaptan and NaOMe or NaH) is added to A-3 and carried through the sequences of Charts A and B to give compounds such as A-5 and B-7 in which cycloalkyl-S- and alkyl-S-replace aryl-S-.

The syntheses of key intermediates C-4A and C-5 are shown in Chart C. Commercial L-malic acid is converted to the halide C-2 via the method of Larcheveque and Petit, Tet. Letters, 25: 3705 (1984) and references cited therein. Reaction of C-2 with thiophenoxide anion (generated from thiophenol and base) gives ester C-3. Ester C-3 is hydrolyzed with aqueous NaOH in MeOH, followed by acidification, to give acid C-3A. Acid C-3A is converted to the O-acetate with Ac$_2$O in pyridine to give C-4A. Coupling of C-3A with His(Tos)-Leu [CH(OH)CH$_2$]Val-IIe-AMP using DEPC and Et$_3$N in CH$_2$Cl$_2$, followed by removal of the tosyl group with 1-HOBT, gives C-5A. Compound C-3 is converted to the carbamate derivate C-4 with diethyl carbamoyl chloride, NaH, Et$_3$N, and THF. Compound C-4 is hydrolyzed to the acid with aqueous NaOH in MeOH, followed by acidification. Coupling of C-5 with His(Tos)-Leu ¥ [CH(OH)CH$_2$]Val-IIe-AMP using DEPC and Et$_3$N in CH$_2$Cl$_2$, followed by removal of the tosyl group with 1-HOBT in MeOH, gives C-6. In a similar manner, ther mercaptide anions, cycloalkyl-S$^-$ and alkyl-S$^-$ (from the mercaptan and a base such as NaOMe and NaH), may be added to C-2 and carried through the above sequence to give compounds of the general structures C-5A and C-6 with cycloalkyl-S- and alkyl-S- replacing aryl-S-.

The synthesis of D-5 is outlined in Chart D. Reaction of thiophenoxide anion with ethyl acrylate gives ester D-2. Hydrolysis of D-2 with aqueous NaOH and MeOH, followed by acidification, gives acid D-3. Coupling of D-3 with His(Tos)-Leu ¥ [CH(OH)CH$_2$]Val-IIe-AMP using DEPC and Et$_3$N in CH$_2$Cl$_2$, followed by removal of the tosyl group with 1-HOBT in MeOH, gives D-5.

Chart E outlines the synthesis of intermediates for the preparation of compounds of this invention wherein X is R$_6$-(CH$_2$)$_i$-C(O)-from known (commercially available) halo ester E-1 or halo ester E-3. Halo ester E-1 is reacted with the mercaptide anion of R$_6$SH to give thio ether E-2, which is hydrolyzed to give acid E-S. Alternatively halo acid E-3 is converted to a salt such as the sodium salt E-4 which is reacted with the anion of R$_6$SH followed by acidification to give acid E-5. In the same manner as the conversion of D-3 to D-5, E-5 may be incorporated into peptides of this invention, e.g., D-5.

DESCRIPTION OF THE PREFERRED EMBODIMENTS

The following Preparations and Examples illustrate the present invention.

In the Preparations and Examples below and throughout this document:
DMF is dimethylformamide,
MsCl is methanesulfonyl chloride,
Et$_3$N is triethylamine,
CH$_2$Cl$_2$ is methylene chloride,
MeOH is methanol,
TFA is trifluoroacetic acid,
DEPC is diethylcyanophosphonate,
1-HOBT is 1-hydroxybenzotriazole,
TBDMS is tert-butyldimethylsilyl,
Tos is p-toluenesulfonyl,
His(Tos) is histidyl protected on the imidazole nitrogen with Tos,
Ac$_2$O is acetic anhydride,
pyr is pyridine,
THF is tetrahydrofuran,
AMP is (2-pyridinyl)methylamino,
DCC is dicyclohexylcarbodiimide,
NaHCO$_3$ is sodium bicarbonate, and
Na$_2$SO$_4$ is sodium sulfate.

PREPARATION 1

Boc-Serine Methyl Ester

Chart A (A-1 to A-2)

A mixture of 2.05 g (0.010 moles) of Boc-L-Ser, 3.27 ml (0.050 moles) in MeI, 1.68 g (0.020 moles) of NaHCO$_3$, and 25 ml of DMF is stirred overnight at room temperature. DMF is removed in vacuo and the residue is extracted with EtOAc, H$_2$O, and brine. The organic layers are filtered through Na$_2$SO$_4$, concentrated, and chromatographed on silica gel using 2% MeOH-CH$_2$Cl$_2$ to give 2.03 g (93%) of titled product.

TLC (4% MeOH-CH$_2$Cl$_2$): Rf is 0.41.

$^1$H-NMR (CDCl$_3$): δ 1.45, s, 9H; 2.52, t, 1 H; 3.78, s, 3H; 3.91, m, 2H; 4.30, m, 1 H; 5.45, bd, 1 H.

PREPARATION 2

Boc-(R,S)-3-(Phenylthio)alanine Methyl Ester

Chart A (A-2 to A-3 to A-4)

To Boc-Ser-OCH$_3$ (0.099 g, 0.451 mmoles) and Et$_3$N (0.069 ml, 0.497 mmoles) in 3 ml of CH$_2$Cl$_2$ at 0° is added 0.038 ml (0.497 mmoles) of methanesulfonyl chloride. After 2¼ hours, an additional 0.07 ml (0.5 mmoles) of Et$_3$N is added and the ice bath is removed. After stirring an additional 1⅔ hours, the reaction mixture is extracted with CH$_2$Cl$_2$, H$_2$O, and brine. The organic layers are filtered through Na$_2$SO$_4$, concentrated and chromatographed on silica gel to give 0.0723 g (80%) of methylene intermediate A-3 (Rf is 0.61, 20% EtOAc-hexane).

A solution of 0.0723 g (0.358 mmoles) of the methylene intermediate, 0.043 g (0.393 mmoles) of thiophenol, 4 drops of Et$_3$N, and 15 ml of MeOH is stirred overnight. MeOH is then removed in vacuo and the residue kept under high vacuum for several hours to give 0.1096 g (98%) of titled product.

TLC (20% EtOAc-hexane): Rf is 0.38.

$^1$H-NMR (CDCl$_3$): δ 1.41, s, 9 H; 3.36, d, 2H; 3.54, s, 3 H; 4.50, m, 1 H; 5.25, bd, 1H; 7.3, m, 5H.

PREPARATION 3

Boc-(R,S)-3-(Phenylthio)alanine

Chart A (A-4 to A-5)

To a solution of 0.100 g (0.321 mmoles) of the ester of Preparation 2 in 3-4 ml of MeOH is added dropwise 0.48 ml of 1N NaOH (exotherm). After stirring for 1 hour, MeOH is removed in vacuo and the residue is extracted with $CH_2Cl_2$ and 2N NCl. The organic layers are filtered through $Na_2SO_4$ and taken to dryness in vacuo to give 0.0828 g (87%) of product. Crystallization from $CH_2Cl_2$-hexane gives 0.07 g of product, mp. 104°-106°.

TLC (4% $MeOH$-$CH_2Cl_2$-HOAc): Rf is 0.30.

Mass spec.: m/z at 297 (theory, 297).

Calcd for $C_{14}H_{19}NO_4S$: C, 56.54; H, 6.44; N, 4.71. Found: C, 56.40; H, 6.58; N, 4.60.

$^1$H-NMR ($CDCl_3$) δ 1.42, s; 1.35, m; 1.4, m; 5.45, bd; 7.3, m.

PREPARATION 5

Boc-ILe-AMP

Chart B (B-1+B-2 to B-3)

To 3.15 g (0.0136 moles) of Boc-Ile and 2.08 g (0.0136 moles) of 1-HOBT in 50 ml of $CH_2Cl_2$ is added 1.34 g (0.0123 moles) of 2-(aminomethyl)pyridine. After 5–10 minutes, 2.81 g (0.0136 moles) of DCC is added. After 35 minutes, DCU is filtered off and the filtrate is washed with aqueous $NaHCO_3$. The organic layers are filtered through $Na_2SO_4$, concentrated re-filtered to remove DCU, and chromatographed on silica gel using 4% $MeOH/CH_2Cl_2$ to give 3.94 g (100%) of product. The solid is crystallized from EtOAc/hexane to give the titled product: 2.28 g of a first crop, m.p. 102°–103.5° C., and 1.50 g of second and third crops.

Calcd. for $C_{17}N_{27}N_3O_3$: C, 63.52; H, 8.47; N, 13.07. Found: C, 63.37; H, 8.55; N, 12.86.

1H-NMR ($CDCl_3$): δ 0.89–0.97, m; 1.43, s, Boc; 1.76, s; 4.0, m, α-CH; 4.56, d (J=5.1), $CH_2Py$; 5.05, d, NH; 7.0–8.5, m, aromatic.

PREPARATION 6

Boc-Leu ¥[CH(OH)$CH_2$]Val-ILe-AMP

B-3 to B-4

Boc-Ile-AMP (1.60 g, 4.98 mmoles) and 50% TFA-$CH_2Cl_2$ (20 ml) is stirred for 30 minutes, after which TFA and $CH_2Cl_2$ are removed in vacuo. The residue is exhustively extracted with $CH_2Cl_2$ and aq. $NaHCO_3$. The organic layers are filtered through $Na_2SO_4$ and taken to dryness.

To a solution of 0.0509 g (0.114 mmoles) of Boc-Leu [CH(OTBDMS)$CH_2$]Val-OH, 0.0253 (0.114 mmoles) of Ile-AMP, and 0.0154 g (0.114 mmoles) of 1-HOBT in 3 ml of $CH_2Cl_2$ is added 0.0235 g (0.114 mmoles) of DCC. After stirring over the weekend (reaction over much sooner), DCU is filtered off and the filtrate is extracted with $CH_2Cl_2$ and aq $NaHCO_3$. The organic layers are filtered through $Na_2SO_4$, concentrated, and the crude product is chromatographed on silica gel using 3% $MeOH$-$CH_2Cl_2$ ($NH_4OH$ sat'd) to give 0.0630 g (85%) of product.

TLC (4% $MeOH$—$CH_2Cl_2$): Rf is 0.14.

$^1$H-NMR ($CDCl_3$): δ 0.11, s; 0.90, s; 0.83–0.95, m; 1.43, s; 3.1, m; 4.5, m; 6.10, bd; 7.1–7.8, m; 9.03, bd.

PREPARATION 7

Boc-His(Tos)-Leu ¥[CH(OTBDMS)$CH_2$]Val-ILe-AMP

B-4 t B-5

A solution of 0.063 g (0.097 mmoles) of B-4 from Preparation 6 in 5 ml of TFA—$CH_2Cl_2$ (1:1) is stirred for 15 minutes at room temperature and then concentrated in vacuo. The residue is extracted with $CH_2Cl_2$ and aq. $NaHCO_3$ and the organic layers are filtered through $Na_2SO_4$ and concentrated to dryness. To this is added Boc-His(Tos)-OH (0.06 g, 0.146 mmoles) and 4 ml of $CH_2Cl_2$, followed by 0.030 g (0.146 mmoles) of DCC. After stirring 2.5 hours at room temperature, DCU is filtered off and the filtrate is concentrated. EtOAc is added and DCU is filtered off again. The filtrate is concentrated and the residue is chromatographed on silica gel using 2% $MeOH$-$CH_2Cl_2$→4% $MeOH$-$CH_2Cl_2$ ($NH_4OH$ sat'd) to give 0.0793 g (87%) of the titled product.

$^1$H-NMR ($CDCl_3$): δ 0.07, s; 0.88–0.95, m; 1.40, s; 2.42, s; 5.95, bd; 6.20, bd; 6.65, bd; 7.05–8.5, m.

TLC (4% $MeOH$-$CH_2Cl_2$-$NH_4OH$ sat'd): Rf is 0.38.

PREPARATION 8

His(Tos)-Leu ¥[CH(OH)$CH_2$]Val-ILe-AMP

B-5 to B-6

A solution of 0.079 g (0.084 mmoles) of B-5 from Preparation 7 in 10 ml of TFA-$CH_2Cl_2$ (1:1) is stirred for 4 hours at room temperature. TFA and $CH_2Cl_2$ are then removed in vacuo and the residue is extracted with $CH_2Cl_2$ and aq $NaHCO_3$. The organic layers are filtered through $Na_2SO_4$ and concentrated. The crude product is chromatographed on silica gel (10 g) using 6% $MeOH$-$CH_2Cl_2$ ($NH_4OH$ sat'd) to give 0.0513 g (84%) of the titled product.

TLC (8% $MeOH$-$CH_2Cl_2$-$NH_4OH$): Rf is 0.40.

EXAMPLE 1

Boc-((S-phenyl)-DL-Cys)-His-Leu ¥[CH(OH)$CH_2$]-Val-ILe-AMP

B-6 to B-7

To 0.0056 g (0.0187 mmoles) of Boc-(R,S)-3(phenylthio)alanine (A-5 from Preparation 3) and 0.0091 g (0.0125 mmoles) of B-6 from Preparation 8 in 3 ml of $CH_2Cl_2$ is added 0.0039 g (0.0187 mmoles) of DCC. After stirring for 30 minutes, the reaction mixture is chromatographed on silica gel (10 g) using 6% $MeOH$-$CH_2Cl_2$ ($NH_4OH$ sat'd) to give 12.7 mg of the (impure) Tos-protected titled product (Rf is 0.42 in 8% $MeOH$—$CH_2Cl_2$—$NH_4OH$). This Tos-protected material is stirred for 2 days with 0.02 g of 1-HOBT in 1 ml of MeOH, after which MeOH is removed in vacuo. The residue is chromatographed on silica gel (10 g) using 6% $MeOH$—$CH_2Cl_2$ ($NH_4OH$ sat'd) to give 0.0077 g of the titled product.

TLC (6% $MeOH$-$CH_2Cl_2$-$NH_4OH$): Rf is 0.11.

FAB mass spec.: [M+H] at m/z 851 (cald'd 851).

$^1$-NMR ($CDCl_3$) for the Tos-protected titled product: δ 1.40, s; 1.43, s (Boc group of each isomer); 2.42 bs (tosyl $CH_3$).

HPLC: Brownlee $C_{18}$ column, phosphate pH 3 buffer: 50% A-50% B, k' is 8.3 (broad), 94.3% purity; flow rate 1.5 ml/min, A 0.1,225 nM.

PREPARATION 9

Ethyl 3-(Phenylthio)propionate

A solution of 0.203 g (1.84 mmoles) of thiophenol, 0.182 g (1.82 mmoles) of ethyl acrylate, 5 drops of Et$_3$N, and 5 ml of EtOH was stirred at room temperature for 3 hours. The mixture is then taken to dryness in vacuo to give 0.372 g of product (clear liquid).

TLC (10% EtOAc-hexane): Rf is 0.44.

$^1$H-NMR (CDCl$_3$): δ 1.24, t, 3 H; 2.60, complex t 2 H; 3.16, complex t, 2 H; 4.14, q, 2H; 7.3, m, 5H.

PREPARATION 10

3-(Phenylthio)propionic acid

To a solution of 0.143 g (0.68 mmoles) of ethyl 3-(phenylthio)propionate in 5 ml of MeOH is added dropwise 0.816 ml (0.816 mmoles) of 1N NaOH. After 35 minutes, MeOH is removed in vacuo and the aqueous residue is extracted with hexane and H$_2$O. The hexane layer is removed and discarded and the aqueous layer is acidified with 0.27 ml of 3N HCl. The aqueous mixture is extracted with EtOAc (backwashed with brine) and organic layers are filtered through Na$_2$SO$_4$ and taken to dryness in vacuo to give 0.1044 g (84%) of product. Crystallization from EtOAc-hexane gives (1st and 2nd crops) 0.066 g of the titled product, m.p. 59.5–60.0°.

TLC (20% EtOAc-hexane): slight movement off baseline.

Mass spec.: m/z at 182.

Calc'd for C$_9$H$_{10}$O$_2$S: C, 59.31; H, 5.53. Found: C, 59.02; H, 5.51.

$^1$H-NMR (CDCl$_3$): δ 2.66, complex t, 2H; 3.16, complex t, 2H; 7.3, m, 5H.

EXAMPLE 2

3-(Phenylthio)propionyl-His-Leu [CH(OH)CH$_2$]Val-Ile-AMP

A mixture of 0.0139 g (0.0763 mmoles) of 3-(phenylthio)propionic acid, 0.0503 g (0.0694 mmoles) of His(-Tos)-Leu [CH(OH)CH$_2$]Val-Ile-AMP, 0.0126 ml (0.0832 mmoles) of DEPC, 0.0116 ml (0.0832 mmoles) of Et$_3$N, and 3 ml of CH$_2$Cl$_2$ is stirred at room temperature for 2 hours. The reaction is extracted with CHCl$_3$ and aq. NaHCO$_3$ and the organic layers are filtered through Na$_2$SO$_4$ and concentrated. CH$_2$Cl$_2$ and hexane are added to the residue and, after cooling in the refrigerator, the solvent is decanted. The remaining solid is stirred for 40 hours with 0.031 g of 1-HOBT in 30 ml of MeOH and 5 ml of CH$_2$Cl$_2$. The solvents are then removed in vacuo and extraction with CHCL$_3$-aq.-NaHCO$_3$ is attempted. This results in a bad precipitation of product (mostly suspended in the aqueous phase). The CHCl$_3$ layer is removed and the aqueous suspension is centrifuged and decanted. The pellet is centrifuged twice with H$_2$O and the remaining solid is absorbed onto silica gel and chromatographed on silica gel (10 g) using 8% MeOH-CH$_2$Cl$_2$ (NH$_4$OH sat'd) to give 0.0352 g of the titled compound.

TLC (8% MeOH-CH$_2$Cl$_2$-NH$_4$OH): Rf is 0.16.

FAB mass spec.: [M+H] measured: 736.4211; theory: 736.4220.

HPLC: pH 3 phosphate buffer, Brownlee C$_{18}$ column: 60% A-40% B, k' is 5.8, 100% purity; 225 nM, A 0.1, flow rate 1.5 ml/min.

EXAMPLE 3

(Phenylthio)acetyl-His-Leu Ψ[CH(OH)CH$_2$]Val-Ile-AMP

Using methods described herein, the titled compound is prepared.

FAB mass spec.: [M+H] measured: 722.404; 722.4063.

CHART A

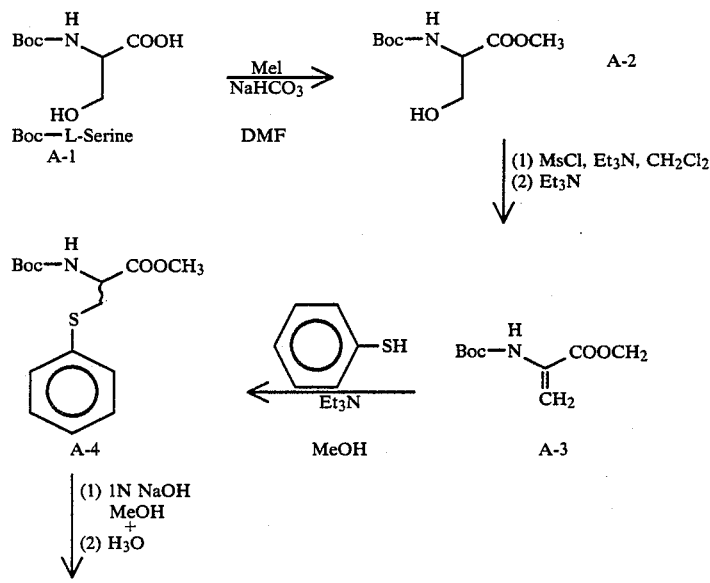

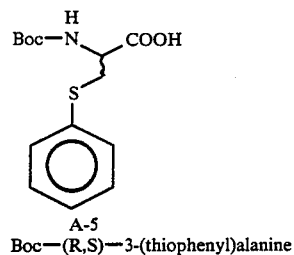
A-5
Boc—(R,S)—3-(thiophenyl)alanine
CHART B
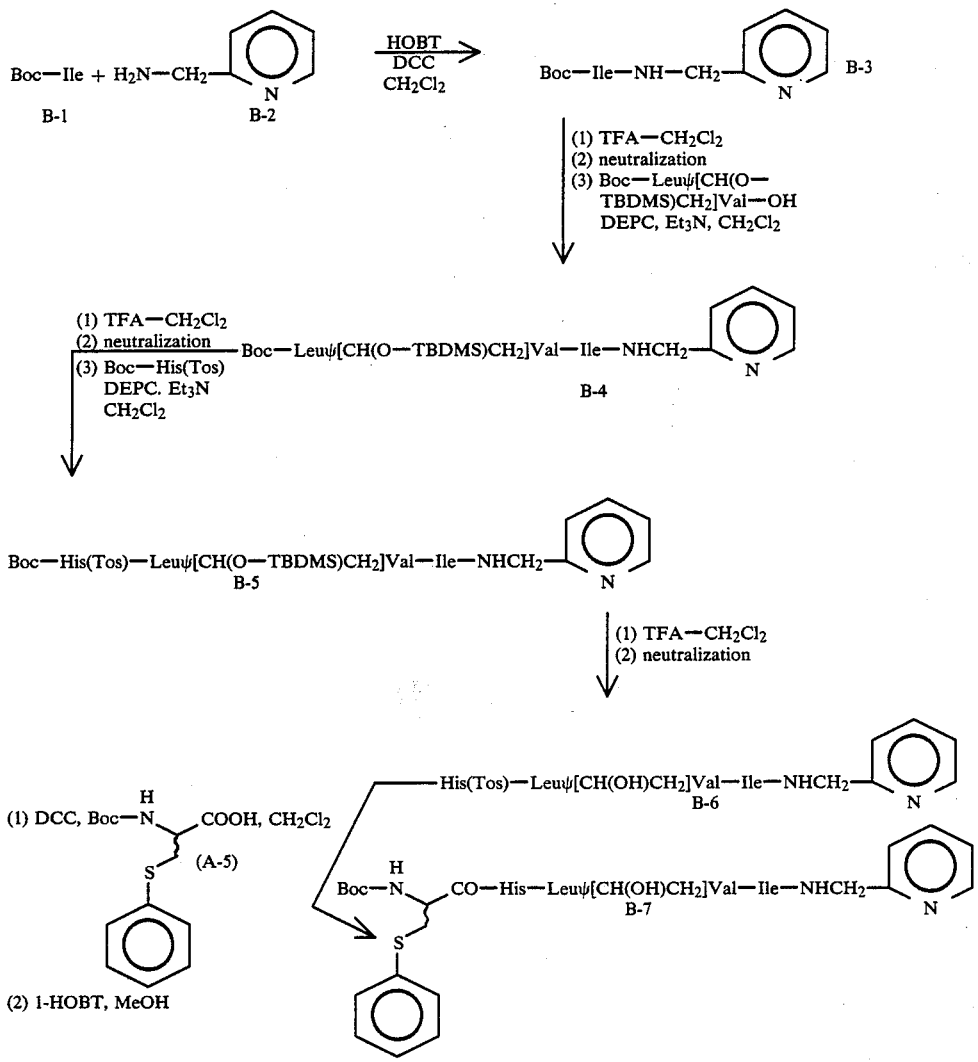
CHART C
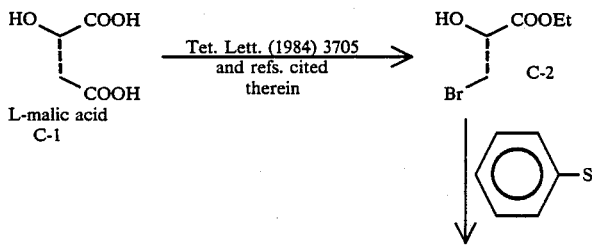

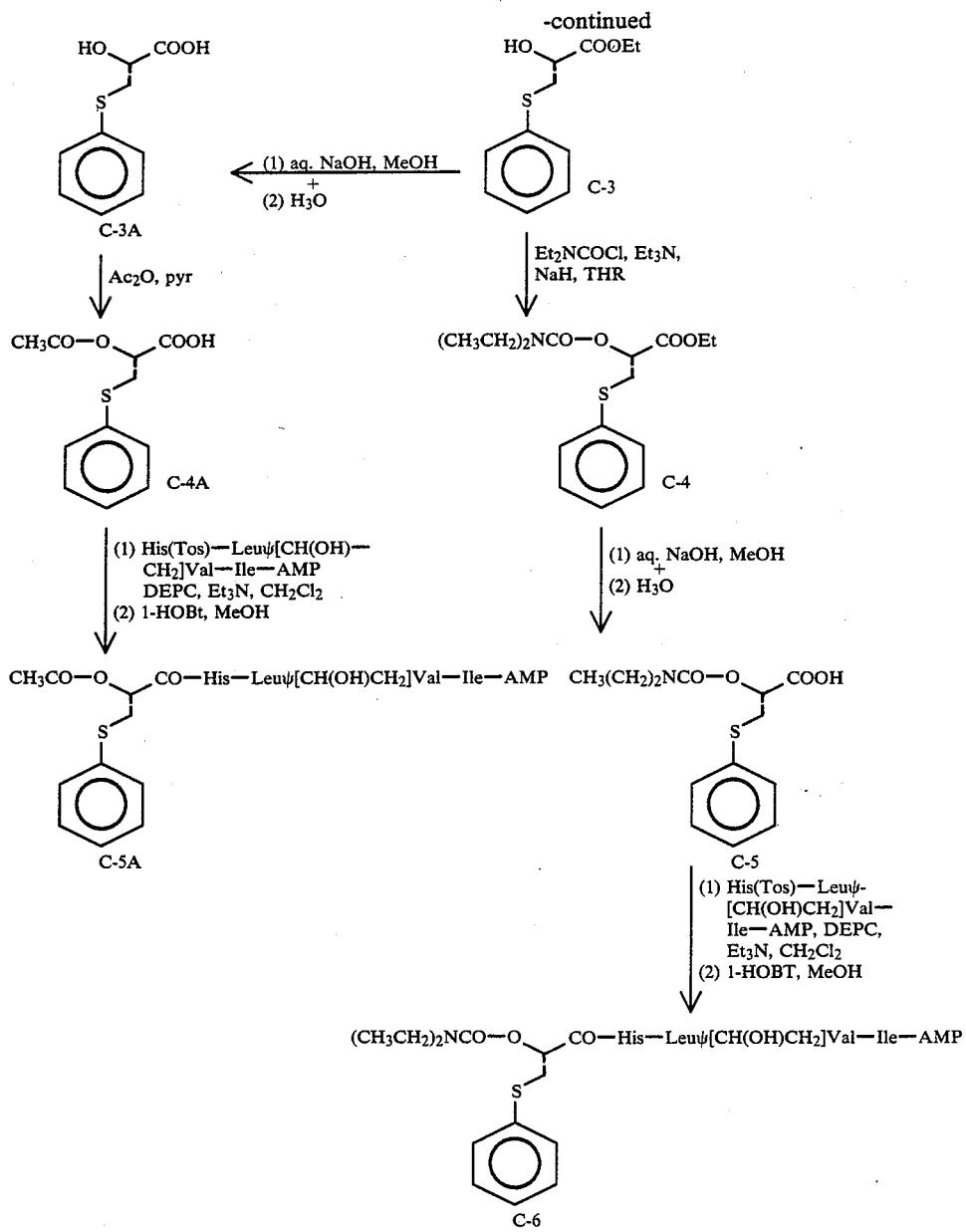
CHART D
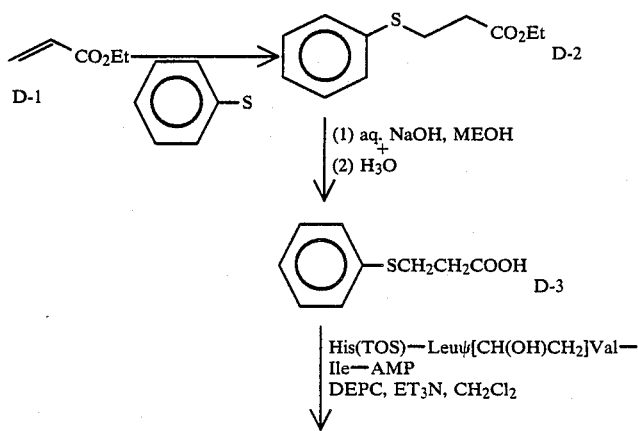

-continued

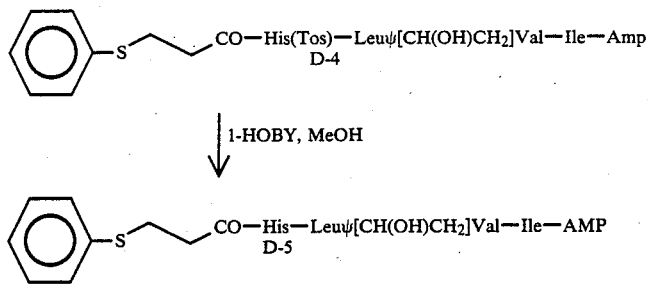

↓ 1-HOBY, MeOH

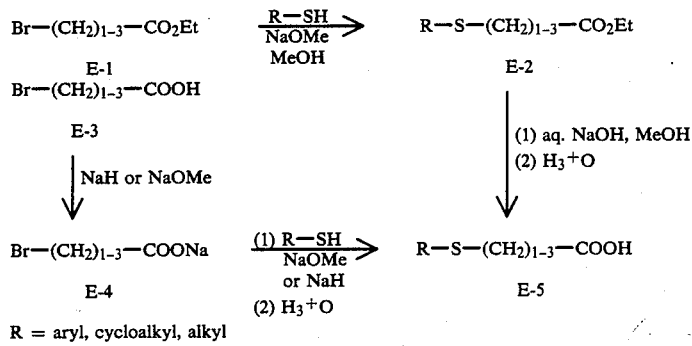

CHART E

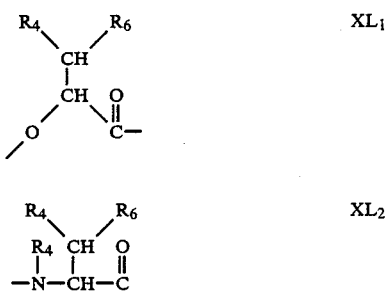

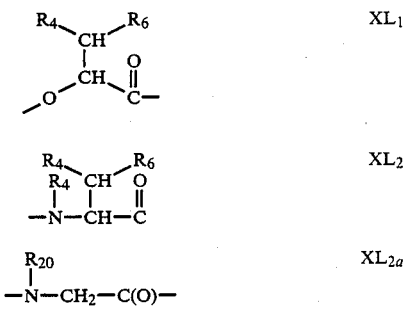

R = aryl, cycloalkyl, alkyl

I claim:

1. A renin inhibitory peptide, having a stable transition state insert corresponding to the 10,11 position of the renin substrate, and additionally having a moiety of the formula $XL_1$ or $XL_2$ corresponding to the 8-position of the renin substrate

[Structure $XL_1$]

[Structure $XL_2$]

wherein $R_4$ at each occurrence is the same or different and is
  (a) hydrogen, or
  (b) $C_1$-$C_5$ alkyl; and
wherein $R_6$ is
  (a) —S—aryl,
  (b) —S—$C_3$-$C_7$ cycloalkyl, or
  (c) —S—$C_1$-$C_5$ alkyl.

2. A renin inhibitory peptide of claim 1 of the formula X-$A_6$-$B_7$-$C_8$-$D_9$-$E_1$-O-$F_{11}$-$G_{12}$-$H_{13}$-$I_{14}$-Z,
  wherein X is
  (a) hydrogen,
  (b) $C_1$-$C_5$ alkyl
  (c) $R_5$—O—$CH_2$—C(O)—,
  (d) $R_5$—$CH_2$—O—C(O)—,
  (e) $R_5$—O—C(O)—,
  (f) $R_5$—$(CH_2)_n$—C(O)—,
  (g) $R_4N(R_4)$—$(CH_2)_n$—C(O),
  (h) $R_5$—$SO_2$—$(CH_2)_q$—C(O)—, or
  (i) $R_5$—$SO_2$—$(CH_2)_q$—O—C(O)$;
wherein $A_6$ is absent or a divalent moiety of the formula $XL_1$, $XL_2$, or $XL_{2a}$

[Structure $XL_1$]

[Structure $XL_2$]

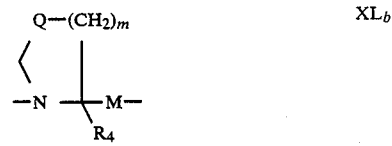

wherein $B_7$ is absent or a divalent moiety of the formula $XL_b$

wherein $C_8$ is a divalent moiety of the formula $XL_1$ or $XL_2$,

[Structure $XL_1$]

-continued

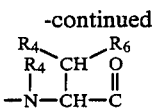      XL₂ wherein D₉ is absent or a divalent moiety of the formula XL₃ or XL₂ₐ,

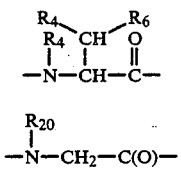

wherein E₁₀-F₁₁ is a divalent moiety of the formula XL₆, XL₆ₐ, XL₆b, XL₆c, XL₆d, or XL₆e,

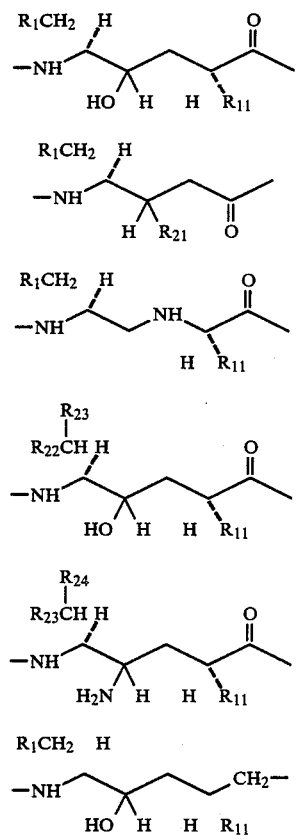

wherein * indicates an asymmetric center which is either in the R or S configuration;
wherein G₁₂ is absent or a divalent moiety of the formula XL₄ or XL₄ₐ

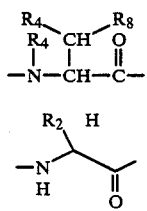

wherein H₁₃ is absent or a divalent moiety of the formula XL₄

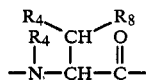  XL₄ wherein I₁₄ is absent or a divalent moiety of the formula XL₅

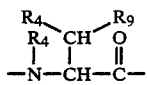  XL₅ wherein Z is
  (a) —O—R₁₀, p2 (b) —N(R₄)R₁₄, or
  (c) C₄-C₈cyclic amino;
wherein R is
  (a) isopropyl,
  (b) isobutyl, p2 (c) phenylmethyl, or p2 (d) C₃-C₇-cycloalkyl;
wherein R₁ is
  (a) hydrogen,
  (b) C₁-C₅alkyl,
  (c) aryl,
  (d) C₃-C₇cycloalkyl, p2 (e) -Het,
  (f) C₁-C₃alkoxy, or
  (g) C₁-C₃alkylthio; p1 wherein R₂ is
  (a) hydrogen, or
  (b) —CH(R₃)R₄;
wherein R₃ is
  (a) hydrogen,
  (b) hydroxy,
  (c) C₁-C₅alkyl,
  (d) C₃-C₇cycloalkyl,
  (e) aryl,
  (f) -Het,
  (g) C₁-C₃alkoxy, or
  (h) C₁-C₃alkylthio;
wherein R₄ at each occurrence is the same or different and is
  (a) hydrogen, or
  (b) C₁-C₅alkyl;
wherein R₅ is
  (a) C₁-C₆alkyl,
  (b) C₃-C₇cycloalkyl,
  (c) aryl,
  (d) -Het, or
  (e) 5-oxo-2-pyrrolidinyl;
wherein R₆ is
  (a) -S-aryl,
  (b) -S-C₃-C₇cycloaclkyl, or
  (c) -S-C₁-C₆alkyl;
wherein R₇ is
  (a) hydrogen,
  (b) C₁-C₅alkyl,
  (c) hydroxy,
  (d) amino C₁-C₄alkyl-,
  (e) guanidinyl C₁-C₃alkyl-,
  (f) aryl,
  (g) -Het,
  (h) methylthio,
  (i) C₃-C₇cycloalkyl, or
  (j) amino;
wherein R₈ is
  (a) hydrogen, (b) $C_1$-$C_5$alkyl,
(c) hydroxy,
(d) aryl,
(e) -Het,
(f) guanidinyl $C_1$-$C_3$alkyl-, or
(g) $C_3$-$C_7$cycloalkyl;

wherein $R_9$ is
(a) hydrogen,
(b) hydroxy,
(c) amino $C_1$-$C_4$alkyl-, or
(d) guanidinyl $C_1$-$C_3$alkyl-;

wherein $R_{10}$ is
(a) hydrogen,
(b) $C_1$-$C_5$alkyl,
(c) —$(CH_2)_n R_{16}$,
(d) —$(CH_2)_n R_{17}$,
(e) $C_3$-$C_7$cycloalkyl,
(f) a pharmaceutically acceptable cation,
(g) —$(CHR_{25})$—$CH_2$—$R_{15}$, or
(h) —$CH_2$—$(CHR_{12})$—$R_{15}$;

wherein $R_{11}$ is —R or —$R_2$;

wherein $R_{12}$ is —$(CH_2)_n$—$R_{13}$;

where $R_{13}$ is
(a) aryl,
(b) amino,
(c) mono-, di or tri-$C_1$-$C_3$alkylamino,
(d) -Het,
(e) $C_1$-$C_5$alkyl
(f) $C_3$-$C_7$cycloalkyl,
(g) $C_1$-$C_5$alkenyl,
(h) $C_3$-$C_7$cycloalkenyl,
(i) hydroxy,
(j) $C_1$-$C_3$alkoxy,
(k) $C_1$-$C_3$alkanoyloxy,
(l) mercapto,
(m) $C_1$-$C_3$alkylthio,
(n) —COOH,
(o) —CO—O—$C_1$-$C_6$alkyl,
(p) —CO—O—$CH_2$—($C_1$-$C_3$alkyl)—N($C_1$-$C_3$alkyl)$_2$,
(q) —CO—$NR_{22}R_{26}$;
(r) $C_4$-$C_7$cyclic amino,
(s) $C_4$-$C_7$cycloalkylamino,
(t) guanidyl,
(u) cyano,
(v) N-cyanoguanidyl,
(w) cyanoamino,
(x) (hydroxy $C_2$-$C_4$alkyl)amino, or
(y) di-(hydroxy$C_2$-$C_4$alkyl)amino;

wherein $R_{14}$ is
(a) hydrogen,
(b) $C_1$-$C_{10}$alkyl,
(c) —$(CH_2)_n$—$R_{18}$,
(d) —$(CH_2)_n$—$R_{19}$,
(e) —$(CHR_{25})$—$CH_2$—$R_{15}$,
(f) —$CH_2$—$(CHR_{12})$—$R_{15}$,
(g) (hydroxy $C_1$-$C_8$alkyl), or
(h) ($C_1$-$C_3$alkoxy)$C_1$-$C_8$alkyl;

wherein $R_{15}$ is
(a) hydroxy,
(b) $C_3$-$C_7$cycloalkyl,
(c) aryl,
(d) amino,
(e) mono-, di-, or tri-$C_1$-$C_3$alkylamino,
(f) mono- or di-[hydroxy $C_2$-$C_4$alkyl]amino,
(g) -Het,
(h) $C_1$-$C_3$alkoxy-,
(i) $C_1$-$C_3$alkanoyloxy-,
(j) mercapto,
(k) $C_1$-$C_3$alkylthio-,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;

wherein $R_{16}$ is
(a) aryl,
(b) amino,
(c) mono- or di-$C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;

wherein $R_{17}$ is
(a) -Het,
(b) $C_{1l}$-$C_5$alkenyl,
(c) $C_3$-$C_7$cycloalkenyl,
(d) $C_1$-$C_3$alkoxy,
(e) mercapto,
(f) $C_1$-$C_3$alkylthio,
(g) —COOH,
(h) —CO—O—$C_1$-$C_6$alkyl,
(i) —CO—O—$CH_2$—($C_1$-$C_3$alkyl)—N($C_1$-$C_3$alkyl)$_2$,
(j) —CO—$NR_{22}R_{26}$,
(k) tri-$C_1$-$C_3$alkylamino,
(l) guanidyl,
(m) cyano,
(n) N-cyanoguanidyl,
(o) (hydroxy $C_2$-$C_4$alkyl)amino,
(p) di-(hydroxy $C_2$-$C_4$alkyl)amino, or
(q) cyanoamino;

wherein $R_{18}$ is
(a) amino,
(b) mono-, or di-$C_1$-$C_3$alkylamino,
(c) $C_4$-$C_7$cyclic amino, or
(d) $C_4$-$C_7$cycloalkylamino;

wherein $R_{19}$ is
(a) aryl,
(b) -Het,
(c) tri-$C_1$-$C_3$alkylamino,
(d) $C_3$-$C_7$cycloalkyl,
(e) $C_1$-$C_5$alkenyl,
(f) $C_3$-$C_7$cycloalkenyl,
(g) hydroxy,
(h) $C_1$-$C_3$alkoxy,
(i) $C_1$-$C_3$alkanoyloxy,
(j) mercapto,
(k) $C_1$-$C_3$alkylthio,
(l) —COOH,
(m) —CO—O—$C_1$-$C_6$alkyl,
(n) —CO—O—$CH_2$—($C_1$-$C_3$alkyl)—N($C_1$-$C_3$alkyl)$_2$,
(o) —CO—$NR_{22}R_{26}$,
(p) guanidyl,
(q) cyano,
(r) N-cyanoguanidyl,
(s) cyanoamino,
(t) (hydroxy $C_2$-$C_4$alkyl)amino,
(u) di-(hydroxy $C_2$-$C_4$alkyl)amino; or
(v) —$SO_3H$;

wherein $R_{20}$ is
(a) hydrogen,
(b) $C_1$-$C_5$alkyl, or
(c) aryl-$C_1$-$C_5$alkyl;

wherein $R_{21}$ is (a) —NH₂, or
(b) —OH;
wherein R₂₂ is
(a) hydrogen, or
(b) $C_1$-$C_3$alkyl;
wherein R₂₃ is
(a) —(CH₂)ₙ—OH,
(b) —(CH₂)ₙ—NH₂,
(c) aryl, or
(d) $C_1$-$C_3$alkyl;
wherein R₂₄ is
(a) —R₁,
(b) —(CH₂)ₙ—OH, or
(c) —(CH₂)ₙ—NH₂;
wherein R₂₅ is —(CH₂)ₙ—R₁₃;
wherein R₂₆ is
(a) hydrogen,
(b) $C_1$-$C_3$alkyl, or
(c) phenyl-$C_1$-$C_3$alkyl;
wherein i is one to three, inclusive;
where m is one or two;
where for each occurrence n is independently an integer of zero to five, inclusive;
wherein p is zero to 2 inclusive;
wherein q is 1 to 5, inclusive;
wherein Q is
(a) —CH₂—,
(b) —CH(OH)—,
(c) —O—, or
(d) —S—; and
wherein M is
(a) —CO—, or
(b) —CH₂—;
wherein aryl is phenyl or naphthyl substituted by zero to 3 of the following:
(a) $C_1$-$C_3$alkyl,
(b) hydroxy,
(c) $C_1$-$C_3$alkoxy,
(d) halo,
(e) amino,
(f) mono- or di-$C_1$-$C_3$alkylamino,
(g) —CHO,
(h) —COOH,
(i) COOR₂₆,
(j) CONHR₂₆,
(k) nitro,
(l) mercapto,
(m) $C_1$-$C_3$alkylthio,
(n) $C_1$-$C_3$alkylsulfinyl,
(o) $C_1$-$C_3$alkysulfonyl,
(p) $C_1$-$C_3$alkylsulfonyl-N(R₄)—
(q) SO₃H,
(r) SO₂NH₂,
(s) —CN, or
(t) —CH₂NH₂;
wherein -Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
(i) $C_1$-$C_6$alkyl,
(ii) hydroxy,
(iii) trifluoromethyl,
(iv) $C_1$-$C_4$alkoxy,
(v) halo,
(vi) aryl,
(vii) aryl $C_1C_4$alkyl-,
(viii) amino, and
(ix) mono- or di-$C_1$-$C_4$alkylamino;
with the overall provisos that
(1) R₁₈ or R₁₉ is hydroxy, mercapto, or amino, or a monosubstituted nitrogen containing group bonded through the nitrogen only when n is not one;
(2) R₁₂ is —(CH₂)ₙ—R₁₃ and n is zero and both R₁₃ and R₁₅ are oxygen-, nitrogen-, or sulfur-containing substituents bonded through the hetero atom, only when the hetero atom is not also bonded to hydrogen;
(3) R₂₅ is —(CH₂)ₙ—R₁₃ and n is zero only when R₁₃ is other than a primary or secondary nitrogen-containing group, hydroxy or mercapto group or when R₄ of —N(R₄)R₁₄ is other than hydrogen; and
(4) R₁₇ or R₁₉ is —COOH only when n for that moiety is other than zero; and
or a carboxy-, amino-, or other reactive group-protected form
or a pharmaceutically acceptable acid addition salt thereof.

3. A compound of claim 2, wherein A, B, H, and I are absent, and $E_{10}F_{11}$ is $XL_6$.

4. Boc-((S-phenyl)-DL-Cys)-His-Leu ¥ [CH(OH)CH₂]Val-Ile-AMP or N-[4-[[N-[N-(1-L-arginyl-L-prolyl)-L-phenylalanyl]-L-histidyl]amino]-3-hydroxy-6-methyl-1-oxyheptyl]-L-isoleucine, tris(trifluoroacetate) (salt), a compound of claim 3.

5. 3-(Phenylthio)propionyl-His-Leu ¥ [CH(OH)CH₂]Val-Ile-AMP, or N-(2-hydroxy-5-methyl-1-(2-methylpropyl)-4-(((2-methyl-1-(((2-pyridinylmethyl)amino)carbonyl)butyl)amino)carbonyl)hexyl)-α-((1-oxo-3-(phenylthio)propyl)amino)-1H-imidazole-4-propanamide, a compound of claim 3.

6. (Phenylthio)acetyl-His-Leu [CH(OH)CH₂]Val-Ile-AMP, a compound of claim 3.

* * * * *